(12) United States Patent
Motegi

(10) Patent No.: US 11,029,270 B2
(45) Date of Patent: Jun. 8, 2021

(54) APPARATUS AND METHOD FOR MEASURING CALORIFIC VALUE

(71) Applicant: Azbil Corporation, Chiyoda-ku (JP)

(72) Inventor: Takahiro Motegi, Chiyoda-ku (JP)

(73) Assignee: Azbil Corporation, Chiyoda-ku (JP)

( * ) Notice: Subject to any disclaimer, the term of this patent is extended or adjusted under 35 U.S.C. 154(b) by 334 days.

(21) Appl. No.: 16/321,652

(22) PCT Filed: Jul. 24, 2017

(86) PCT No.: PCT/JP2017/026611
§ 371 (c)(1),
(2) Date: Jan. 29, 2019

(87) PCT Pub. No.: WO2018/030127
PCT Pub. Date: Feb. 15, 2018

(65) Prior Publication Data
US 2020/0049636 A1 Feb. 13, 2020

(30) Foreign Application Priority Data

Aug. 9, 2016 (JP) .............................. JP2016-156190

(51) Int. Cl.
*G01N 25/20* (2006.01)
(52) U.S. Cl.
CPC .................... *G01N 25/20* (2013.01)
(58) Field of Classification Search
None
See application file for complete search history.

(56) References Cited

U.S. PATENT DOCUMENTS 5,486,107 A 1/1996 Bonne
5,667,300 A 9/1997 Mandelis et al.
(Continued)

FOREIGN PATENT DOCUMENTS

EP 1947450 A1 * 7/2008 ........... G01N 33/225
JP 5075986 B2 11/2012
(Continued)

OTHER PUBLICATIONS

Božiková, Monika & Hlaváč, Peter Thermal Conductivity and Thermal Diffusivity of Biodiesel And Bioethanol Samples. Acta Technologica Agriculturae. 16. 10.2478/ata-2013-0023. 2013 (Year: 2013).*

(Continued)

*Primary Examiner* — Roy Y Yi
(74) *Attorney, Agent, or Firm* — Oblon, McClelland, Maier & Neustadt, L.L.P.

(57) ABSTRACT

A measurement unit (101) acquires a first value serving as a thermal conductivity index and a second value serving as a thermal diffusivity index, with respect to a fuel gas to be measured, at a first temperature, a second temperature, and a third temperature that are different from each other. A change rate calculation unit (102) calculates a temperature change rate $\kappa_1$ of the first value between the first temperature and the second temperature, measured by the measurement unit (101), a temperature change rate $\kappa_2$ of the first value between the second temperature and the third temperature, a temperature change rate $\alpha_1$ of the second value between the first temperature and the second temperature, and a temperature change rate $\alpha_2$ of the second value between the second temperature and the third temperature. A calorific value calculation unit (103) calculates the calorific value of the fuel gas through a calorific value calculation formula in (Continued)

which the $\kappa_1$, $\kappa_2$, $\alpha_1$, and $\alpha_2$ serve as explanatory variables and the calorific value serves as an object variable.

6 Claims, 3 Drawing Sheets

(56) References Cited

U.S. PATENT DOCUMENTS

| | | | |
|---|---|---|---|
| 8,888,361 B2 * | 11/2014 | Ooishi | ................ G01K 17/006 |
| | | | 374/37 |
| 2011/0185789 A1 | 8/2011 | Ooishi et al. | |
| 2016/0138951 A1 | 5/2016 | Pretre | |

FOREIGN PATENT DOCUMENTS

| | | | | |
|---|---|---|---|---|
| JP | 2016-95308 A | 5/2016 | | |
| WO | WO1993008457 | * | 4/1993 | ............. G01N 33/28 |

OTHER PUBLICATIONS

International Search Report dated Oct. 17, 2017 in PCT/JP2017/026611, 2 pages.
"Netsuryo Soklutei • Netsu Bunseki Handbook" The Japan Society of Calorimetry and Thermal Analysis, 1998, 6 pages.
Extended European Search Report dated Feb. 3, 2020 in European Patent Application No. 17839200.7, 9 pages.

* cited by examiner

APPARATUS AND METHOD FOR MEASURING CALORIFIC VALUE

TECHNICAL FIELD

The present invention relates to an apparatus and a method for measuring a calorific value, and more particularly to an apparatus and a method for measuring a calorific value of city gas or other type of gas, predominantly composed of natural gas.

BACKGROUND ART

For example, the city gas is prepared by mixing petroleum gas (PG) in the natural gas (NG), which is the main material, and supplied after the calorific value is adjusted to a predetermined level. A most basic method for measuring the calorific value of such fuel gas is burning the gas, and measuring the calorific value. To measure the calorific value of the fuel gas, the relation between gas density and the calorific value may also be utilized. In addition, a method of calculating the calorific value on the basis of the thermal conductivity of the fuel gas has also been proposed (see PTL 1).

Since the calorific value of a single-component gas can be uniquely identified, the calorific value of a mixed gas can be calculated on the basis of the gas composition when the gas type (components) and the ratio thereof are known. Here, relations between the thermal conductivity and temperature are illustrated in FIG. 7, and relations between the thermal diffusivity and temperature are illustrated in FIG. 8, with respect to some main components of the natural gas.

With the technique according to PTL 1, the calorific value of the mixed gas is calculated without obtaining the ratio of each of the gas components of the gas that is the object of the calorific value measurement. With the mentioned technique, first, a value of heat loss coefficient or thermal conductivity of a plurality of mixed gases is measured at a plurality of temperatures. Then a calorific value calculation formula is generated, on the basis of known calorific values of the plurality of mixed gases and the value of the heat loss coefficient or thermal conductivity measured at the plurality of temperatures, utilizing the heat loss coefficient or thermal conductivity at the plurality of temperatures as the explanatory variables, and the calorific value as the object variable.

With the technique according to PTL 1, the mentioned calorific value calculation formula is utilized to measure the calorific value of a mixed gas to be measured, the calorific value of which is unknown. First, the value of the heat loss coefficient or thermal conductivity of the mixed gas to be measured, the calorific value of which is unknown, is measured at a plurality of temperatures. Then the value of the heat loss coefficient or thermal conductivity of the mixed gas to be measured, measured at the plurality of temperatures, are substituted in the explanatory variables, which are the heat loss coefficient or thermal conductivity at the plurality of temperatures, in the calorific value calculation formula, to calculate the calorific value of the mixed gas to be measured.

CITATION LIST

Patent Literature

PTL 1: Japanese Patent No. 5075986

Non Patent Literature

NPL 1: "Handbook of Calorimetry and Thermal Analysis" edited by The Japan Society of Calorimetry and Thermal Analysis and published by Maruzen-Yushodo Co., Ltd., 2010, Page 104.

SUMMARY OF INVENTION

Technical Problem

With the mentioned technique of calculating the calorific value on the basis of the thermal conductivity, however, the accuracy of the calorific value of the fuel gas obtained from the measurement result of thermal conductivity may be degraded when the composition ratio of the fuel gas fluctuates.

The present invention has been accomplished to minimize the mentioned drawback, and provides a technique to obtain the fuel gas calorific value with higher accuracy despite large fluctuation of the composition ratio.

Solution to Problem

A calorific value measurement apparatus according to the present invention includes a measurement unit that acquires a first value serving as a thermal conductivity index and a second value serving as a thermal diffusivity index, with respect to a fuel gas to be measured, at a first temperature, a second temperature, and a third temperature that are different from each other, a change rate calculation unit that calculates a temperature change rate $\kappa_1$ of the first value between the first temperature and the second temperature, measured by the measurement unit, a temperature change rate $\kappa_2$ of the first value between the second temperature and the third temperature, a temperature change rate $\alpha_1$ of the second value between the first temperature and the second temperature, and a temperature change rate $\alpha_2$ of the second value between the second temperature and the third temperature, and a calorific value calculation unit that calculates the calorific value of the fuel gas through a calorific value calculation formula in which the $\kappa_1$, $\kappa_2$, $\alpha_1$, and $\alpha_2$ serve as explanatory variables and the calorific value serves as an object variable. The calorific value calculation formula is a regression formula obtained through acquiring the first value and the second value, with respect to each of four or more fuel gases the calorific value of which is known, at the first temperature, the second temperature, and the third temperature that are different from each other, acquiring the temperature change rate $\kappa_1$ of the first value between the first temperature and the second temperature, the temperature change rate $\kappa_2$ of the first value between the second temperature and the third temperature, the temperature change rate $\alpha_1$ of the second value between the first temperature and the second temperature, and the temperature change rate $\alpha_2$ of the second value between the second temperature and the third temperature, with respect to the first value and the second value of each of the fuel gases, and utilizing relations between the $\kappa_1$, $\kappa_2$, $\alpha_1$, and $\alpha_2$ of each of the fuel gases serving as the explanatory variables, and the calorific value of each of the known fuel gases serving as the object variable.

In the calorific value measurement apparatus, the measurement unit may include a heat transmitter and a heat receiver, and the first value and the second value may be acquired on a basis of an electrical signal from the heat transmitter and an electrical signal from the heat receiver.

In the calorific value measurement apparatus, the calorific value calculation formula may be a regression formula obtained through preparing, as sample gases, four or more fuel gases the calorific value of which is known, the fuel gases being different in composition ratio of component gases from each other, acquiring values of respective electrical signals from the heat transmitter and the heat receiver, the values depending on a temperature of each of the sample gases prepared, heating the heat transmitter contacted by the sample gas at a plurality of heating temperatures, acquiring values of respective electrical signals from the heat transmitter and the heat receiver at each of the heating temperatures, acquiring the temperature change rates $\kappa_1$, $\kappa_2$, $\alpha_1$, and $\alpha_2$ of the first value and the second value, acquired on a basis of the values of the electrical signals from the heat transmitter and the heat receiver, and utilizing the $\kappa_1$, $\kappa_2$, $\alpha_1$, and $\alpha_2$ as the explanatory variables, and the calorific value of the sample gas as the object variable.

A calorific value measurement method according to the present invention includes a first step including acquiring a first value serving as a thermal conductivity index and a second value serving as a thermal diffusivity index, with respect to a fuel gas to be measured, at a first temperature, a second temperature, and a third temperature that are different from each other, a second step including calculating a temperature change rate $\kappa_1$ of the first value between the first temperature and the second temperature, a temperature change rate $\kappa_2$ of the first value between the second temperature and the third temperature, a temperature change rate $\alpha_1$ of the second value between the first temperature and the second temperature, and a temperature change rate $\alpha_2$ of the second value between the second temperature and the third temperature, and a third step including calculating the calorific value of the fuel gas through a calorific value calculation formula in which the $\kappa_1$, $\kappa_2$, $\alpha_1$, and $\alpha_2$ serve as explanatory variables and the calorific value serves as an object variable. The calorific value calculation formula is a regression formula obtained through acquiring the first value and the second value, with respect to each of four or more fuel gases the calorific value of which is known, at the first temperature, the second temperature, and the third temperature that are different from each other, acquiring the temperature change rate $\kappa_1$ of the first value between the first temperature and the second temperature, the temperature change rate $\kappa_2$ of the first value between the second temperature and the third temperature, the temperature change rate $\alpha_1$ of the second value between the first temperature and the second temperature, and the temperature change rate $\alpha_2$ of the second value between the second temperature and the third temperature, with respect to the first value and the second value of each of the fuel gases, and utilizing relations between the $\kappa_1$, $\kappa_2$, $\alpha_1$, and $\alpha_2$ of each of the fuel gases serving as the explanatory variables, and the calorific value of each of the known fuel gases serving as the object variable.

In the calorific value measurement method, the first value and the second value may be acquired through measurement of the fuel gas using a measurement unit including a heat transmitter and a heat receiver, on a basis of an electrical signal from the heat transmitter and an electrical signal from the heat receiver.

In the calorific value measurement method, the calorific value calculation formula may be obtained through preparing, as sample gases, four or more fuel gases the calorific value of which is known, the fuel gases being different in composition ratio of component gases from each other, acquiring values of respective electrical signals from the heat transmitter and the heat receiver, the values depending on a temperature of each of the sample gases prepared, heating the heat transmitter contacted by the sample gas at a plurality of heating temperatures, acquiring values of respective electrical signals from the heat transmitter and the heat receiver at each of the heating temperatures, acquiring the temperature change rates $\kappa_1$, $\kappa_2$, $\alpha_1$, and $\alpha_2$ of the first value and the second value, acquired on a basis of the values of the electrical signals from the heat transmitter and the heat receiver, and utilizing the $\kappa_1$, $\kappa_2$, $\alpha_1$, and $\alpha_2$ as the explanatory variables, and the calorific value of the sample gas as the object variable.

Advantageous Effects of Invention

The mentioned arrangement according to the present invention provides an excellent effect of enabling the fuel gas calorific value to be more accurately acquired, despite large fluctuation of the composition ratio.

DESCRIPTION OF EMBODIMENTS

As result of diligent studies carried out by the present inventors under the circumstance where further improvement in measurement accuracy is sought for, it has proved that the calorific value can be acquired with high accuracy, by employing a change rate of the physical quantity of a fuel gas, obtained when the temperature changes. The present inventors have found out that the change rate of the first value and the second value, originating from the temperature change, is insusceptible to measurement accuracy, and useful for improvement in accuracy of the calorific value estimation. In the present invention, further, the calorific value calculation formula is generated, using the measured values as explanatory variables, and the calorific value as the object variable. Accordingly, it is not mandatory in the present invention that a true thermal conductivity and a true thermal diffusivity are measured, but it suffices that an index (value), reflecting the true thermal conductivity and the true thermal diffusivity with high reproducibility, is acquired. Thus, the alleviation of restriction to the measurement is another important feature of the present invention.

Figure 1:
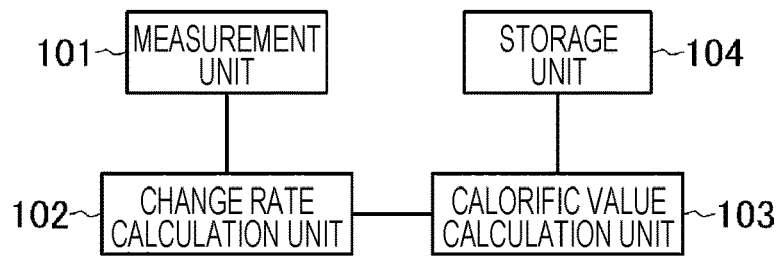
FIG. 1 is a block diagram illustrating a configuration of a calorific value measurement apparatus according to an embodiment of the present invention.

Hereafter, an embodiment of the present invention will be described, with reference to the drawings. FIG. 1 is a block diagram illustrating a configuration of a calorific value measurement apparatus according to the embodiment of the present invention. The apparatus includes a measurement unit 101, a change rate calculation unit 102, a calorific value calculation unit 103, and a storage unit 104. The calorific value measurement apparatus according to this embodiment is a computer device including a central processing unit (CPU), a main storage device, an external storage device, and a network interface, and the above-cited functional units are realized when the CPU operates according to a program installed in the main storage device. Alternatively, the functional units may be dispersed in a plurality of computer devices.

The measurement unit 101 measures a first value and a second value of a fuel gas to be measured, at a first temperature, a second temperature, and a third temperature that are different from each other. The first value serves as an index of the thermal conductivity of the fuel gas to be measured, which is derived, for example, utilizing a predetermined correlation based on the heat loss coefficient of the fuel gas to be measured. The second value serves as an index of the thermal diffusivity of the fuel gas to be measured, which is derived, for example, utilizing a predetermined correlation based on a transitional response of a temperature rise, measured when the fuel gas to be measured is heated. The specific configuration of the measurement unit 101 will be subsequently described.

The change rate calculation unit 102 calculates a temperature change rate $\kappa_1$ of the first value between the first temperature and the second temperature, and a temperature change rate $\kappa_2$ of the first value between the second temperature and the third temperature, on the basis of the first value measured by the measurement unit 101. In addition, the change rate calculation unit 102 calculates a temperature change rate $\alpha_1$ of the second value between the first temperature and the second temperature, and a temperature change rate $\alpha_2$ of the second value between the second temperature and the third temperature, on the basis of the first value measured by the measurement unit 101.

The calorific value calculation unit 103 calculates the calorific value of the fuel gas through a calorific value calculation formula in which the $\kappa_1$, $\kappa_2$, $\alpha_1$, and $\alpha_2$ serve as explanatory variables and the calorific value serves as an object variable. The calorific value calculation formula is stored in the storage unit 104.

Now, the calorific value calculation formula can be expressed as a regression formula obtained as follows. First, the first value and the second value are measured with respect to each of four or more fuel gases, the calorific value of which is known, at the first temperature, the second temperature, and the third temperature that are different from each other. Then the temperature change rate $\kappa_1$ of the first value between the first temperature and the second temperature, and the temperature change rate $\kappa_2$ of the first value between the second temperature and the third temperature are acquired, with respect to each of the fuel gases. In addition, the temperature change rate $\alpha_1$ of the second value between the first temperature and the second temperature, and the temperature change rate $\alpha_2$ of the second value between the second temperature and the third temperature are acquired. Then, the regression formula cited hereunder is derived, utilizing the temperature change rates $\kappa_1$, $\kappa_2$, $\alpha_1$, and $\alpha_2$ of each of the fuel gases as the explanatory variables, and the calorific value of each of the known fuel gases as the object variable. In other words, a coefficient $c_i$ and degrees n1, n2, n3, and n4 in the following regression formula are analytically obtained, on the basis of the known calorific value of each of the fuel gases, and the $\kappa_1$, $\kappa_2$, $\alpha_1$, and $\alpha_2$. In the following formula, $c_i$ represents a coefficient. The degrees may be set, for example, as n1+n2+n3+n4=0 to 3.

$$f(\kappa_1,\kappa_2,\alpha_1,\alpha_2) \Sigma c^i \kappa_1^{n_1} \kappa_2^{n_2} \alpha_1^{n_3} \alpha_2^{n_4} \qquad [\text{Math. 1}]$$

The calorific value of the fuel gas can be calculated, through the calorific value calculation formula derived as above.

Figure 2:
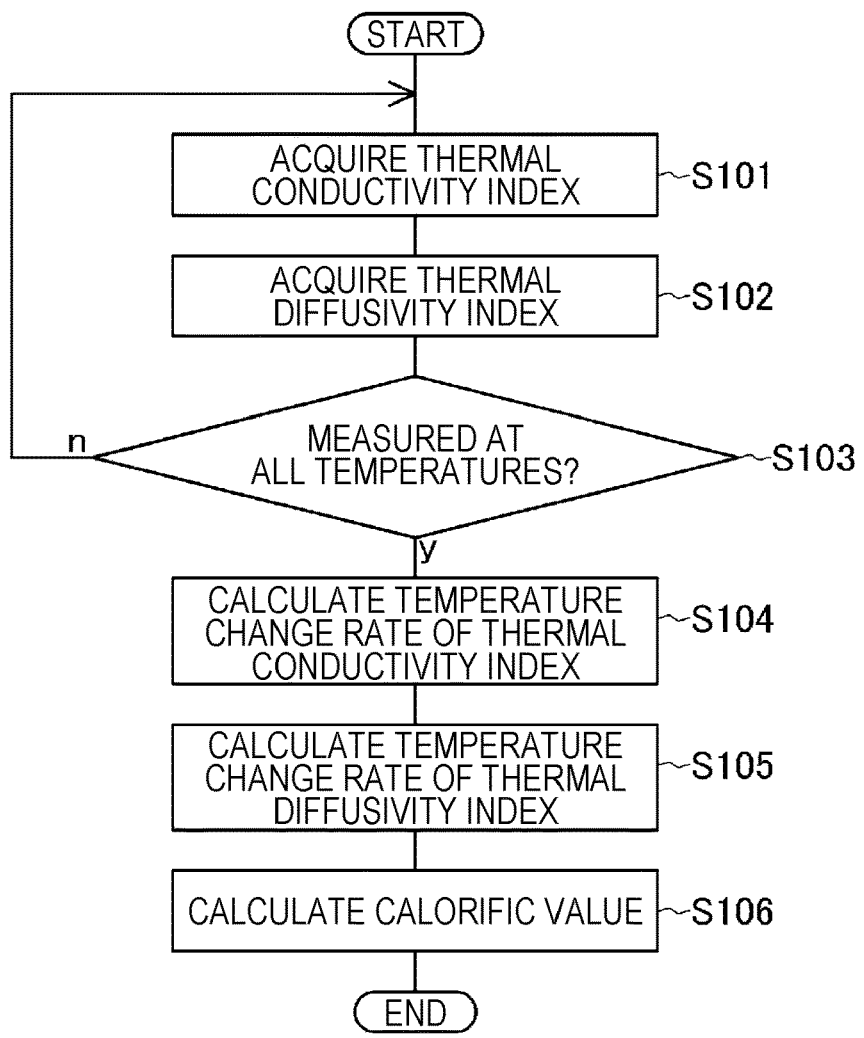
FIG. 2 is a flowchart for explaining a calorific value measurement method according to the embodiment of the present invention.

Hereunder, an example of the operation of the calorific value measurement apparatus (calorific value measurement method) according to the embodiment of the present invention will be described, with reference to the flowchart illustrated in FIG. 2.

First, at step S101, the measurement unit 101 acquires a first value $k_1$ at a first temperature $T_1$. Then the measurement unit 101 acquires a second value $a_1$, at the first temperature $T_1$, at step S102. Likewise, at each of a second temperature $T_2$ and a third temperature $T_3$, the acquisition of the first value and the second value by the measurement unit 101 is performed, the first, second, and third temperatures being different from each other (step S101 to step S103), so that the first value $k_1$ a first value $k_2$, a first value $k_3$, the second value $a_1$, a second value $a_2$, and a second value $a_3$ are acquired.

Then at step S104, the change rate calculation unit 102 acquires the temperature change rate $\kappa_1$ of the first value between the first temperature $T_1$ and the second temperature $T_2$, and the temperature change rate $\kappa_2$ of the first value between the second temperature $T_2$ and the third temperature $T_3$, as indicated hereunder.

[Math. 2]

$$\kappa_1 = \frac{k_2 - k_1}{T_2 - T_1}, \kappa_2 = \frac{k_3 - k_2}{T_3 - T_2} \qquad (1)$$

At step S105, the change rate calculation unit 102 acquires the temperature change rate $\alpha_1$ of the second value between the first temperature $T_1$ and the second temperature $T_2$, and the temperature change rate $\alpha_2$ of the second value between the second temperature $T_2$ and the third temperature $T_2$, as indicated hereunder.

[Math. 3]

$$\alpha_1 = \frac{a_2 - a_1}{T_2 - T_1}, \alpha_2 = \frac{a_3 - a_2}{T_3 - T_2} \qquad (2)$$

Thereafter, at step S106, the calorific value calculation unit 103 calculates the calorific value of the fuel gas, through the calorific value calculation formula in which the $\kappa_1$, $\kappa_2$, $\alpha_1$, and $\alpha_2$ serve as the explanatory variables, and the calorific value serves as the object variable.

Here, the calorific value calculation formula is, as described above, the regression formula obtained from the known calorific value, the temperature change rate $\kappa_1$ of the first value between the first temperature $T_1$ and the second temperature $T_2$, the temperature change rate $\kappa_2$ of the first value between the second temperature $T_2$ and the third temperature $T_3$, the temperature change rate $\alpha_1$ of the second value between the first temperature $T_1$ and the second temperature $T_2$, and the temperature change rate $\alpha_2$ of the second value between the second temperature $T_2$ and the third temperature $T_3$, of each of four or more fuel gases the calorific value of which is known, on the basis of the first value and the second value measured at the first temperature $T_1$, the second temperature $T_2$, and the third temperature $T_3$ that are different from each other, with respect to each of the fuel gases.

With the arrangement according to the embodiment, the gas calorific value can be acquired with higher accuracy, despite large fluctuation of the gas composition of the object to be measured.

The measurement of the first value and the second value will now be described hereunder. To measure these values, the measurement unit including a heat transmitter and a heat receiver is employed, to acquire the first value and the second value on the basis of an electrical signal from the heat transmitter and an electrical signal from the heat receiver, as described below.

Figure 3:
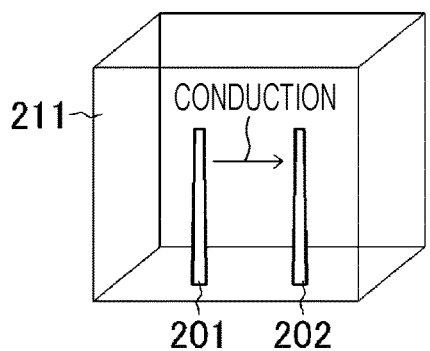
FIG. 3 is a schematic drawing for explaining the concept of measurement of a first value and a second value.

First, the measurement of the first value will be described. To measure the first value, a heat transmitter 201 and a heat receiver 202 are employed to measure an ambient gas 211, for example as illustrated in FIG. 3. The heat transmitter 201 and the heat receiver 202 are resistance temperature detector elements, for example constituted of platinum. The gas 211 is stored, for example, in a measurement chamber of a predetermined processing apparatus, with stabilized gas flow and gas pressure.

It will be assumed that the heat transmitter 201, the heat receiver 202, and the ambient gas 211 are in a steady state at a temperature $T_0$. In this state, the respective electrical resistances of the heat transmitter 201 and the heat receiver 202 accord with each other, at $r_{base}=r_0$ corresponding to the temperature $T_0$.

Figure 4:
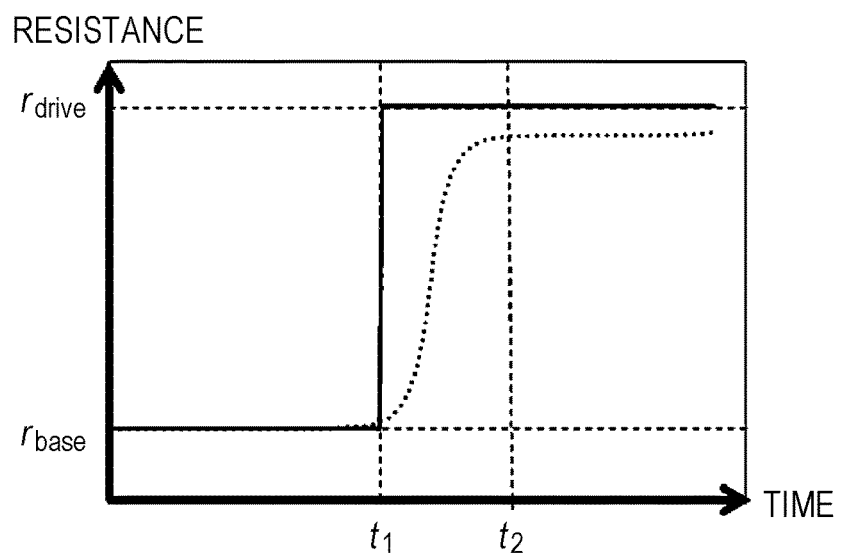
FIG. 4 is a characteristic graph illustrating a change in resistance of a heat transmitter and a heat receiver.

When a current is applied in this state to the heat transmitter 201, for example at a time point $t_1$, so as to make the electrical resistance of the heat transmitter 201 $r_{drive}=r_1$ corresponding to a temperature $T_1$, the temperature (electrical resistance) of the heat receiver 202 assumes a steady state at a time point $t_2$, as illustrated in FIG. 4. In FIG. 4, solid lines represent the change in electrical resistance of the heat transmitter 201, and dot lines represent the change in electrical resistance of the heat receiver 202. In this state, a temperature slope is formed in the gas 211 between the heat transmitter 201 and the heat receiver 202.

As described in PTL 1, a heat loss coefficient can be obtained on the basis of power consumption to drive the heat transmitter 201 to attain the temperature $T_1$, and a difference in temperature between the heat transmitter 201 and the heat receiver 202. It is known that the heat loss coefficient is correlated with the first value of the gas at the temperature $T_1$. Therefore, a value obtained on the basis of the mentioned correlation, from the heat loss coefficient acquired when the heat transmitter 201 is driven to the temperature $T_1$, is taken as the first value $k_1$ at the temperature $T_1$.

The measurement of the second value will be described hereunder. When the heat transmitter 201, the heat receiver 202, and the gas 211 are in the steady state at the temperature $T_1$, the respective electrical resistances of the heat transmitter 201 and the heat receiver 202 accord with each other, at $r_{base}=r_1$ corresponding to the temperature $T_1$.

In this state a current is applied, for example at the time point $t_1$ so as to raise the temperature of the heat transmitter 201 by $\Delta T$ (electrical resistance that realizes temperature $T_1+\Delta T$ corresponds to the $r_{drive}$).

It is widely known, through observation of the temperature of the gas 211 with the heat receiver 202 upon heating the gas 211 with the heat transmitter 201, that a transitional response of the temperature rise observed at the heat receiver 202 and the second value of the gas 211 are correlated with each other (see NPL 1). Examples of parameters for evaluating the transitional response include the following.

Time constant of the transitional response of the temperature rise of the heat receiver 202;

Time until the temperature of the heat receiver 202 rises by a certain amount after the heat transmitter 201 starts the heating; and Temperature of heat receiver 202 measured when a certain period of time has elapsed after the heat transmitter 201 started the heating.

Accordingly, a value obtained on the basis of the correlation, from the parameter (indices cited above, such as the time constant) for measuring the transitional response of the temperature (electrical resistance) of the heat receiver 202, when the temperature of the heat transmitter 201 is raised by $\Delta T$, after the heat transmitter 201, the heat receiver 202, and the gas 211 entered the steady state at the temperature T1, is taken as the second value $a_1$ at the temperature $T_1$.

Hereunder, the temperature change rate will be described. As stated above, the first value $k_2$ and the second value $a_2$ at the temperature $T_2$, and the first value $k_3$ and the second value $a_3$ at the temperature $T_3$ are acquired, in the same manner as acquiring the first value $k_1$ and the second value $a_1$ at the temperature $T_1$. On the basis of the values acquired as above, the $\kappa_1$, $\kappa_2$, $\alpha_3$, and $\alpha_2$ are acquired, according to the equations (1) and (2) cited earlier.

The generation of the calorific value calculation formula will now be described hereunder. To generate the calorific value calculation formula, for example, four or more gases, the calorific value of which is known, are utilized to acquire the $\kappa_1$, $\kappa_2$, $\alpha_1$, and $\alpha_2$ of each of the gases. A plurality of sample gases each containing, for example, oxygen gas, nitrogen gas, carbon dioxide gas, methane gas, ethane gas, propane gas, and butane gas, but in different composition ratios, are prepared. Then the $\kappa_1$, $\kappa_2$, $\alpha_3$, $\alpha_2$ are acquired, with respect to each of the plurality of sample gases prepared. The calorific value of each of the plurality of sample gases is known.

Regarding the sample gases prepared as above, the composition ratio (Table 1), and the measurement results with respect to the corresponding composition (Table 2) are indicated hereunder. The numerals in the tables represent a percentage in volume.

TABLE 1

| Sample Composition | | | | | | | |
|---|---|---|---|---|---|---|---|
| Sample | Oxygen | Nitrogen | Carbon Dioxide | Methane | Ethane | Propane | Butane |
| 1 | 0 | 3 | 9 | 88.00 | 0 | 0 | 0 |
| 2 | 0.2 | 6 | 6 | 82.80 | 3 | 2 | 0 |

TABLE 1-continued

Sample Composition

| Sample | Oxygen | Nitrogen | Carbon Dioxide | Methane | Ethane | Propane | Butane |
|---|---|---|---|---|---|---|---|
| 3 | 0.2 | 6 | 3 | 85.80 | 3 | 2 | 0 |
| 4 | 0 | 3 | 3 | 76.00 | 18 | 0 | 0 |
| 5 | 0 | 12 | 6 | 72.00 | 6 | 4 | 0 |
| 6 | 0.2 | 15 | 9 | 69.80 | 3 | 2 | 1 |
| 7 | 0 | 3 | 6 | 71.00 | 15 | 4 | 1 |
| 8 | 0.2 | 3 | 3 | 72.80 | 18 | 2 | 1 |
| 9 | 0.2 | 9 | 3 | 76.80 | 9 | 2 | 0 |
| 10 | 0.2 | 12 | 0 | 73.80 | 6 | 6 | 2 |

TABLE 2

Measurement Result

| | 75° C. | | 125° C. | | 175° C. | | Temperature Change Rate | | | | Calorific |
|---|---|---|---|---|---|---|---|---|---|---|---|
| Sample | $\kappa_1$ | $\alpha_1$ | $\kappa_2$ | $\alpha_2$ | $\kappa_3$ | $\alpha_3$ | $K_1$ | $K_2$ | $\alpha_1$ | $\alpha_2$ | Value |
| 1 | 38.78 | 29.01 | 46.37 | 37.57 | 54.59 | 47.07 | 0.152 | 0.164 | 0.171 | 0.190 | 35.13 |
| 2 | 38.07 | 27.57 | 45.58 | 35.66 | 53.72 | 44.64 | 0.150 | 0.163 | 0.162 | 0.180 | 37.20 |
| 3 | 38.77 | 28.12 | 46.42 | 36.34 | 54.72 | 45.47 | 0.153 | 0.166 | 0.164 | 0.183 | 38.40 |
| 4 | 37.19 | 25.32 | 44.96 | 32.81 | 53.41 | 41.15 | 0.155 | 0.169 | 0.150 | 0.167 | 43.02 |
| 5 | 36.41 | 25.68 | 43.61 | 33.19 | 51.38 | 41.55 | 0.144 | 0.155 | 0.150 | 0.167 | 37.03 |
| 6 | 36.03 | 26.08 | 42.97 | 33.72 | 50.43 | 42.21 | 0.139 | 0.149 | 0.153 | 0.170 | 33.35 |
| 7 | 35.66 | 23.14 | 43.19 | 29.99 | 51.37 | 37.63 | 0.151 | 0.164 | 0.137 | 0.153 | 44.31 |
| 8 | 36.32 | 23.77 | 44.00 | 30.80 | 52.37 | 38.64 | 0.154 | 0.167 | 0.141 | 0.157 | 45.11 |
| 9 | 37.44 | 26.46 | 44.93 | 34.22 | 53.04 | 42.84 | 0.150 | 0.162 | 0.155 | 0.172 | 39.03 |
| 10 | 36.55 | 24.34 | 43.88 | 31.41 | 51.84 | 39.28 | 0.147 | 0.159 | 0.141 | 0.157 | 42.46 |

A regression formula is generated with respect to each of the gases by multi-variable analysis, on the basis of a plurality of relations in which the $\kappa_1$, $\kappa_2$, $\alpha_1$, $\alpha_2$ serve as the explanatory variables, and the known calorific value of each of the fuel gases serves as the object variable. The multi-variable analysis applicable to the generation of the regression formula may be, for example, a support vector regression. The regression formula generated as above may be stored in the storage unit 104, as the calorific value calculation formula.

Although ten types of gases are utilized, to obtain the regression formula on the basis of the ten relations in which the $\kappa_1$, $\kappa_2$, $\alpha_1$, $\alpha_2$ serve as the explanatory variables and the known calorific value of each of the fuel gases serves as the object variable in the foregoing example, a different method may be adopted. Generating the regression formula from a wider range of gases further improves statistical reliability of the calorific value, acquired through the regression formula (calorific value calculation formula) thus generated.

The arrangement according to the embodiment enables the calorific value to be acquired with higher accuracy, for example compared with the technique according to PTL 1. Here, the acquisition of the calorific value will be studied, with respect to 2172 types of mixed gases (fuel gases) each containing, for example, methane gas in a variation range of 68 to 100%, ethane gas in a variation range of 0 to 24%, propane gas in a variation range of 0 to 6%, butane gas in a variation range of 0 to 3%, oxygen gas in a variation range of 0 to 0.2%, nitrogen gas in a variation range of 0 to 15%, and carbon dioxide gas in a variation range of 0 to 9%.

According to the embodiment, 343 types of mixed gases were selected as the sample gases out of the 2172 types of mixed gases, the composition ratio of which largely varies, and a regression formula was generated with respect to each of the sample gases by multi-variable analysis, on the basis of a plurality of relations in which the $\kappa_1$, $\kappa_2$, $\alpha_1$, $\alpha_2$ serve as the explanatory variables, and the calorific value of each of the sample gases serves as the object variable.

As a comparative example, the first values $k_1$, $k_2$, $k_3$, $k_4$, and $k_5$ were acquired with respect to each of the fuel gases, at five temperatures different from each other, as described in PTL 1, and a regression formula was generated by multi-variable analysis, on the basis of a plurality of relations in which the first value $k_1$, $k_2$, $k_3$, $k_4$, and $k_5$ acquired as above serve as the explanatory variables, and the calorific value of each of the sample gases serves as the object variable.

Figure 5:
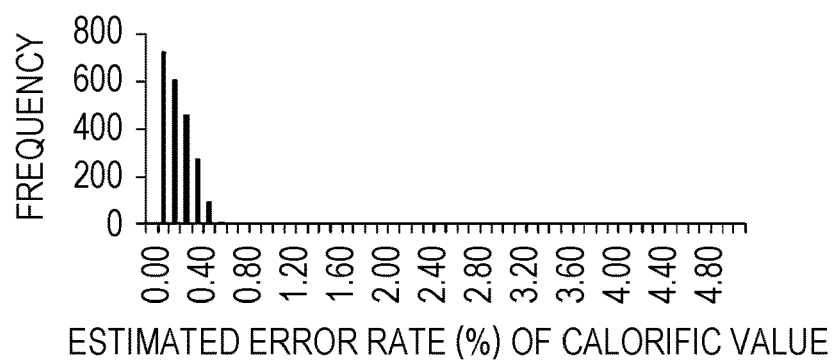
FIG. 5 is a characteristic graph illustrating deviations in calculation result of calorific value obtained by a regression formula according to the embodiment, with respect to 2172 types of mixed gases.
Figure 6:
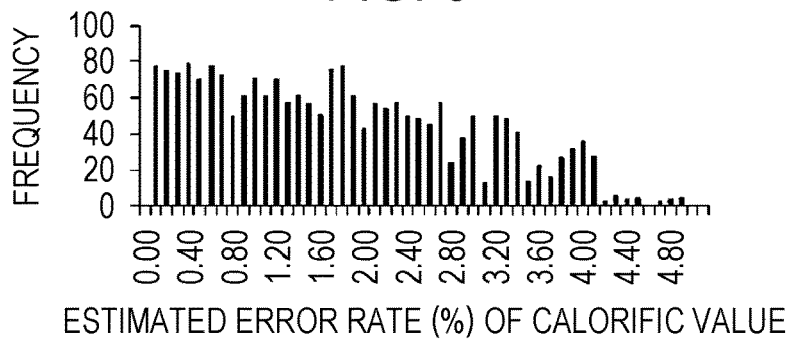
FIG. 6 is a characteristic graph illustrating deviations in calculation result of calorific value obtained by a regression formula according to a comparative example, with respect to 2172 types of mixed gases.
Figure 7:
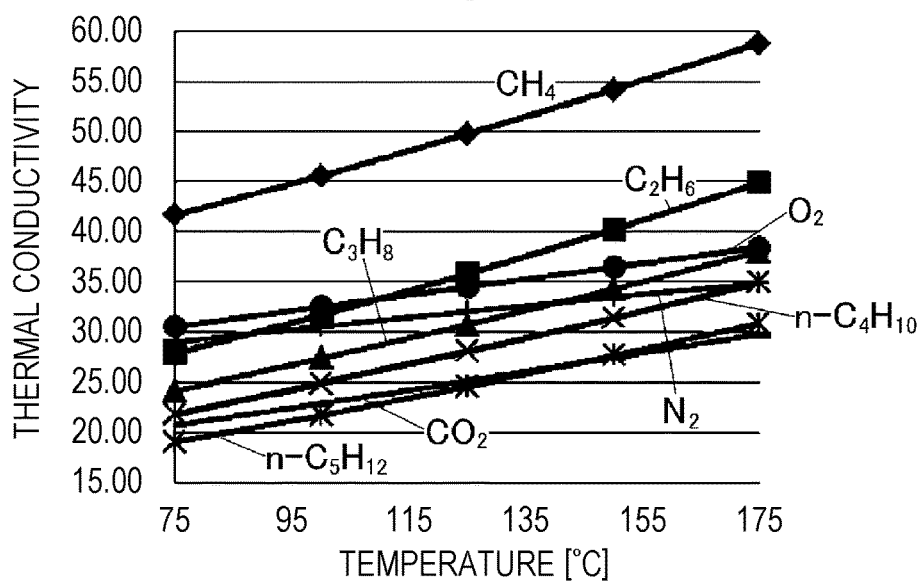
FIG. 7 is a characteristic graph illustrating a relation between temperature and thermal conductivity, with respect to main components of natural gas.
Figure 8:
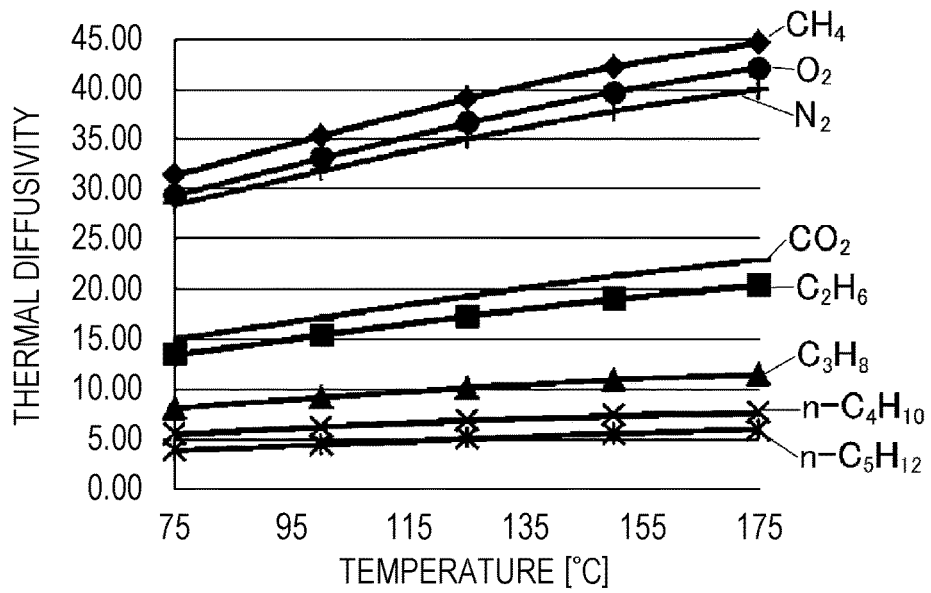
FIG. 8 is a characteristic graph illustrating a relation between temperature and thermal diffusivity, with respect to main components of natural gas.

The variation in accuracy (estimated error rate) in the acquisition result of the calorific value with the regression formula according to the embodiment, with respect to each of the 2172 types of mixed gases (fuel gases), has proved to be narrow, as illustrated in FIG. 5. In contrast, the variation in accuracy in the acquisition result of the calorific value with the regression formula according to the comparative example, with respect to each of the 2172 types of mixed gases (fuel gases), has proved to be large, as illustrated in FIG. 6.

According to the present invention, as described thus far, the calorific value is acquired through the calorific value calculation formula, in which the temperature change rate of the first value and the temperature change rate of the second value serve as the explanatory variables, and the calorific value of the fuel gas serves as the object variable. Therefore, the gas calorific value can be acquired with higher accuracy, despite large fluctuation of the composition ratio.

It should be noted that the present invention is in no way limited to the foregoing embodiment. It is obvious that various modifications and combinations may be made by those skilled in the art, within the technical scope of the present invention.

REFERENCE SIGNS LIST 101 measurement unit
102 change rate calculation unit
103 calorific value calculation unit
104 storage unit

The invention claimed is:
1. A calorific value measurement method comprising:
a first step including acquiring a first value serving as a thermal conductivity index and a second value serving as a thermal diffusivity index, with respect to a fuel gas to be measured, at a first temperature, a second temperature, and a third temperature that are different from each other;

a second step including calculating a temperature change rate $\kappa_1$ of the first value between the first temperature and the second temperature, a temperature change rate $\kappa_2$ of the first value between the second temperature and the third temperature, a temperature change rate $\alpha_1$ of the second value between the first temperature and the second temperature, and a temperature change rate $\alpha_2$ of the second value between the second temperature and the third temperature; and a third step including calculating a calorific value of the fuel gas through a calorific value calculation formula in which the $\kappa_1$, $\kappa_2$, $\alpha_1$, and $\alpha_2$ serve as explanatory variables and the calorific value serves as an object variable, wherein the calorific value calculation formula is a regression formula obtained through acquiring the first value and the second value, with respect to each of four or more fuel gases the calorific value of which is known, at the first temperature, the second temperature, and the third temperature that are different from each other, acquiring the temperature change rate $\kappa_1$ of the first value between the first temperature and the second temperature, the temperature change rate $\kappa_2$ of the first value between the second temperature and the third temperature, the temperature change rate $\alpha_1$ of the second value between the first temperature and the second temperature, and the temperature change rate $\alpha_2$ of the second value between the second temperature and the third temperature, with respect to the first value and the second value of each of the fuel gases, and utilizing relations between the $\kappa_1$, $\kappa_2$, $\alpha_1$, and $\alpha_2$ of each of the fuel gases serving as the explanatory variables, and the calorific value of each of the known fuel gases serving as the object variable.

2. The calorific value measurement method according to claim 1, wherein the first value and the second value are acquired through measurement of the fuel gas using a measurement unit including a heat transmitter and a heat receiver, on a basis of an electrical signal from the heat transmitter and an electrical signal from the heat receiver.

3. The calorific value measurement method according to claim 2, wherein the calorific value calculation formula is obtained through:

preparing, as sample gases, four or more fuel gases the calorific value of which is known, the fuel gases being different in composition ratio of component gases from each other;

acquiring values of respective electrical signals from the heat transmitter and the heat receiver, the values depending on a temperature of each of the sample gases prepared;

heating the heat transmitter contacted by the sample gas at a plurality of heating temperatures;

acquiring values of respective electrical signals from the heat transmitter and the heat receiver at each of the heating temperatures;

acquiring the temperature change rates $\kappa_1$, $\kappa_2$, $\alpha_1$, and $\alpha_2$ of the first value and the second value, acquired on a basis of the values of the electrical signals from the heat transmitter and the heat receiver; and utilizing the $\kappa_1$, $\kappa_2$, $\alpha_1$, and $\alpha_2$ as the explanatory variables, and the calorific value of the sample gas as the object variable.

4. A calorific value measurement apparatus comprising:

a measurement unit configured to acquire a first value serving as a thermal conductivity index and a second value serving as a thermal diffusivity index, with respect to a fuel gas to be measured, at a first temperature, a second temperature, and a third temperature that are different from each other;

a change rate calculation unit configured to calculate a temperature change rate $\kappa_1$ of the first value between the first temperature and the second temperature, measured by the measurement unit, a temperature change rate $\kappa_2$ of the first value between the second temperature and the third temperature, a temperature change rate $\alpha_1$ of the second value between the first temperature and the second temperature, and a temperature change rate $\alpha_2$ of the second value between the second temperature and the third temperature; and a calorific value calculation unit configured to calculate a calorific value of the fuel gas through a calorific value calculation formula in which the $\kappa_1$, $\kappa_2$, $\alpha_1$, and $\alpha_2$ serve as explanatory variables and the calorific value serves as an object variable, wherein the calorific value calculation formula is a regression formula obtained through acquiring the first value and the second value, with respect to each of four or more fuel gases the calorific value of which is known, at the first temperature, the second temperature, and the third temperature that are different from each other, acquiring the temperature change rate $\kappa_1$ of the first value between the first temperature and the second temperature, the temperature change rate $\kappa_2$ of the first value between the second temperature and the third temperature, the temperature change rate $\alpha_1$ of the second value between the first temperature and the second temperature, and the temperature change rate $\alpha_2$ of the second value between the second temperature and the third temperature, with respect to the first value and the second value of each of the fuel gases, and utilizing relations between the $\kappa_1$, $\kappa_2$, $\alpha_1$, and $\alpha_2$ of each of the fuel gases serving as the explanatory variables, and the calorific value of each of the known fuel gases serving as the object variable.

5. The calorific value measurement apparatus according to claim 4, wherein the measurement unit includes a heat transmitter and a heat receiver, and the first value and the second value are acquired on a basis of an electrical signal from the heat transmitter and an electrical signal from the heat receiver.

6. The calorific value measurement apparatus according to claim 5, wherein the calorific value calculation formula is a regression formula obtained through:

preparing, as sample gases, four or more fuel gases the calorific value of which is known, the fuel gases being different in composition ratio of component gases from each other;

acquiring values of respective electrical signals from the heat transmitter and the heat receiver, the values depending on a temperature of each of the sample gases prepared;

heating the heat transmitter contacted by the sample gas at a plurality of heating temperatures;

acquiring values of respective electrical signals from the heat transmitter and the heat receiver at each of the heating temperatures;

acquiring the temperature change rates $\kappa_1$, $\kappa_2$, $\alpha_1$, and $\alpha_2$ of the first value and the second value, acquired on a basis of the values of the electrical signals from the heat transmitter and the heat receiver; and utilizing the $\kappa_1$, $\kappa_2$, $\alpha_1$, and $\alpha_2$ as the explanatory variables, and the calorific value of the sample gas as the object variable.

* * * * *